United States Patent [19]

Kodera

[11] 4,085,738
[45] Apr. 25, 1978

[54] AUTOMATIC DISEASE-DETECTING TREATMENT APPARATUS FOR THE SPINE

[76] Inventor: Katsuji Kodera, 35-12, Wada 1-chome, Suginami, Tokyo, Japan

[21] Appl. No.: 774,653

[22] Filed: Mar. 4, 1977

[30] Foreign Application Priority Data

Jul. 23, 1976 Japan .............................. 51-087176

[51] Int. Cl.² ........................... A61B 5/00; A61F 5/00
[52] U.S. Cl. .................................. 128/2 N; 128/52; 128/70
[58] Field of Search .................................. 128/68–71, 128/25, 33, 51, 52, 2 N

[56] References Cited

U.S. PATENT DOCUMENTS

| | | | |
|---|---|---|---|
| 1,173,306 | 2/1916 | Pool | 128/71 |
| 1,529,872 | 3/1925 | Craig | 128/71 |
| 1,978,223 | 10/1934 | Parker | 128/70 |
| 2,035,869 | 3/1936 | Denison | 128/71 |
| 2,646,035 | 7/1953 | Anderson | 128/2 N |
| 4,036,213 | 7/1977 | Gregory | 128/2 S |

Primary Examiner—Lawrence W. Trapp
Attorney, Agent, or Firm—Wenderoth, Lind & Ponack

[57] ABSTRACT

An automatic disease-detecting treatment apparatus for the spine comprising a mobile bed which moves in a longitudinal direction on a machine base, an adjustable head-rest at one end of the mobile bed, two adjustable cross-pieces mounted at intervals parallel to the longitudinal direction of the mobile bed, a plurality of pressure rods of an adjustable mounting height which form covered pressure members at the tips, an angular cam which engages with the pressure rods at the rods' lower surface and which moves longitudinally in the direction of the mobile bed's movement, a flexible member fixed at one end to said head-rest of the mobile bed and at the other to the machine base, a plurality of indicator plates on the flexible member arranged in accordance with the positions of human organs. The indicator plates show each of these human organs and a pointer is provided at the angular cam which moves longitudinally at the back of the flexible member. This apparatus can detect the place where a patient has an internal disease and at the same time offers massaging and "Shiatsu" (Japanese finger-press massage) treatment.

13 Claims, 15 Drawing Figures

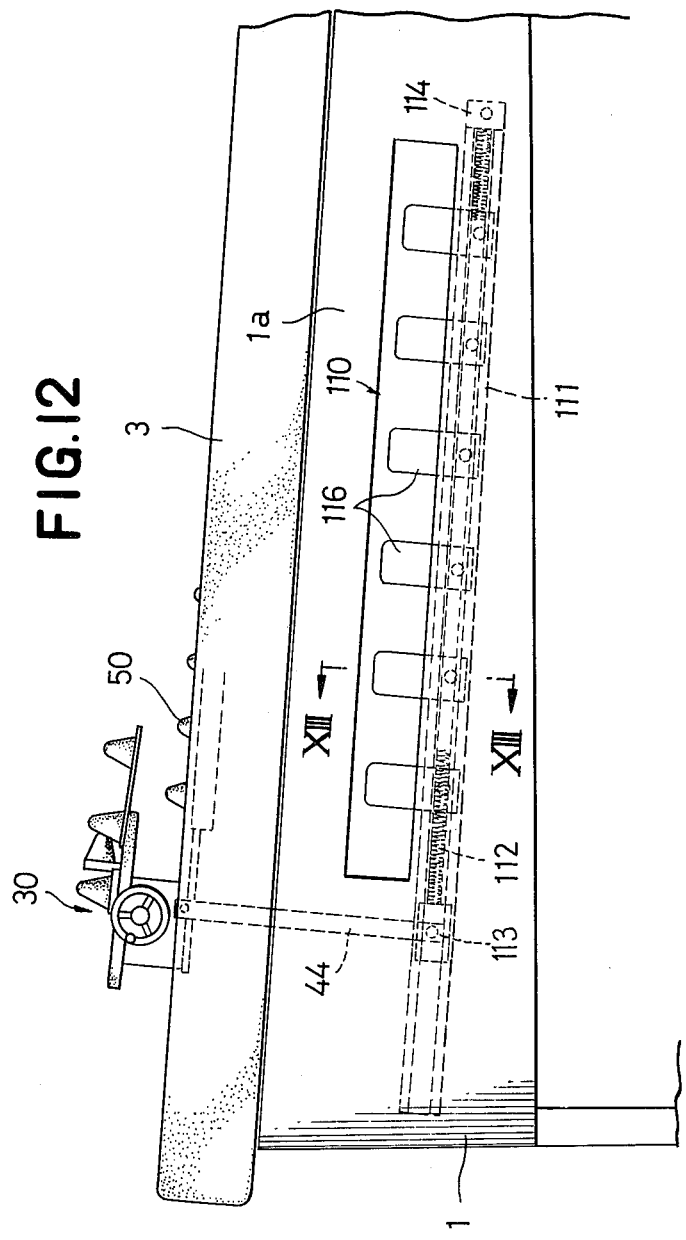
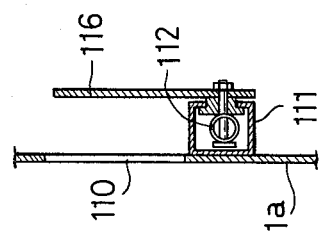

AUTOMATIC DISEASE-DETECTING TREATMENT APPARATUS FOR THE SPINE

BACKGROUND OF THE INVENTION

The present invention concerns a medical apparatus which automatically detects diseases of the visceral organs and performs a massage of the spine.

The visceral organs of man are located at fixed points in the body, irrespective of the size of an individual. If a person has a disease of any visceral organ, he may experience pain in a certain area along the vertebra and/or experience a heat sensation in the said area. The present inventor has studied this subject for many years and has deduced a theorem from various cases which he has clinically attended.

DESCRIPTION OF THE PRIOR ART

Heretofore, an apparatus was available which would have the patient take a recumbent position on rollers or eccentric rotating bodies and perform massage of the spine by the motion of the said rollers or eccentric rotating bodies. However, such apparatus did not achieve sufficient therapeutic results. There was, however, no apparatus of this type or a massaging machine which could be used to detect a disease of visceral organs.

SUMMARY OF THE INVENTION

One of the objects of the present invention is to provide an apparatus for detecting diseases of the visceral organs by applying a pressure member against both sides of the spine and pushing the said pressure member upward.

Another object of the present invention is to provide an apparatus which would help the patient keep his spine in a normal position by moving the patient parallel to the spine in a reciprocal movement and allowing the pressure member to perform massage and SHIATSU, i.e. a Japanese finger pressing massage.

Still another object of the present invention is to provide a diagnostic, therapeutic apparatus for patients of various heights by providing a movable head-rest on a mobile bed upon which the patient assumes a recumbent position.

DESCRIPTION OF THE DRAWINGS

The details of the present invention will now be explained by referring to the attached drawings in which:

FIG. 12 is a frontal view of the automatic diagnostic mechanism;

FIG. 13 is a cross-sectional view along the line XIII—XIII of FIG. 12;

DESCRIPTION OF THE PREFERRED EMBODIMENTS

Figure 1:
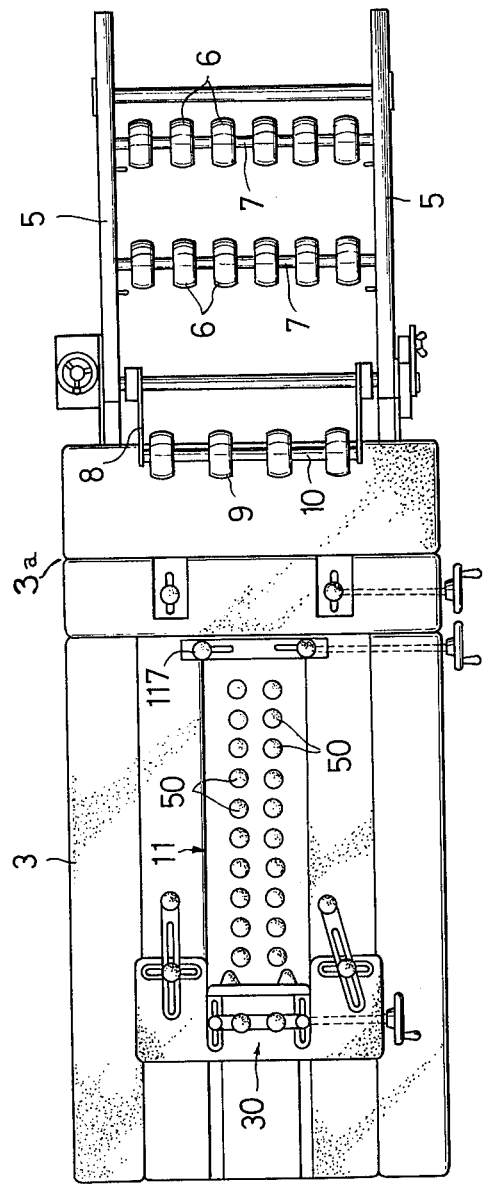
FIG. 1 is a plan view of the medical apparatus in accordance with present invention.
Figure 2:
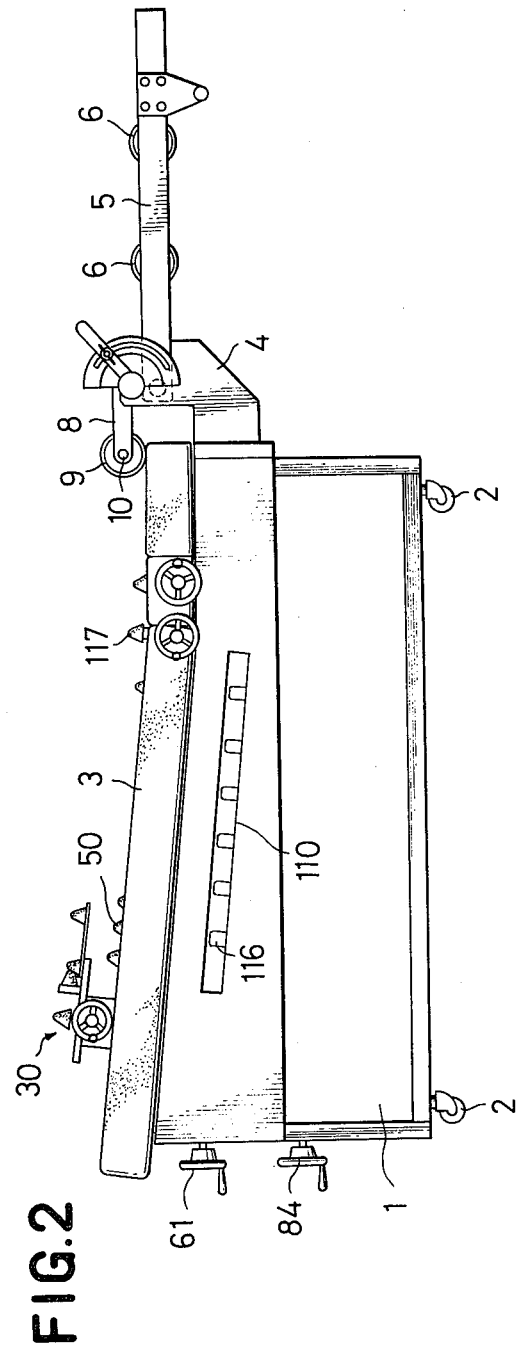
FIG. 2 is a side view of the same.

In the drawings, 1 denotes a box-like machine base which is provided with casters 2 at its bottom for setting the apparatus at an arbitrary position. On top of the machine base 1 is placed a mobile bed 3 in such a position as to allow reciprocal movement in the longitudinal direction. At one end of the mobile stand 3 is formed a hip-rest 3a while at the other end is provided an adjustable head-rest 30. Two bearing plates 4 attached to the side of the machine base 1, where the hip-rest 3a of the said mobile bed 3 is provided, and screwed with support rods 5 having freely adjustable angles. There are placed over and screwed to the said rods the roller axes 7 attached with foot-rest rollers 6. To the said bearing plates 4 are screwed arms 8 also with freely adjustable angles and the said arms 8 have roller axis 10 screwed thereto having thigh-rest rollers 9. These two types of rollers 6 and 9 are made of rubber or materials similar to rubber.

At the center in the longitudinal direction of the said mobile bed 3 is a hole 11 and two rows of plural pressure members 50 are provided along this hole 11.

Figure 3:
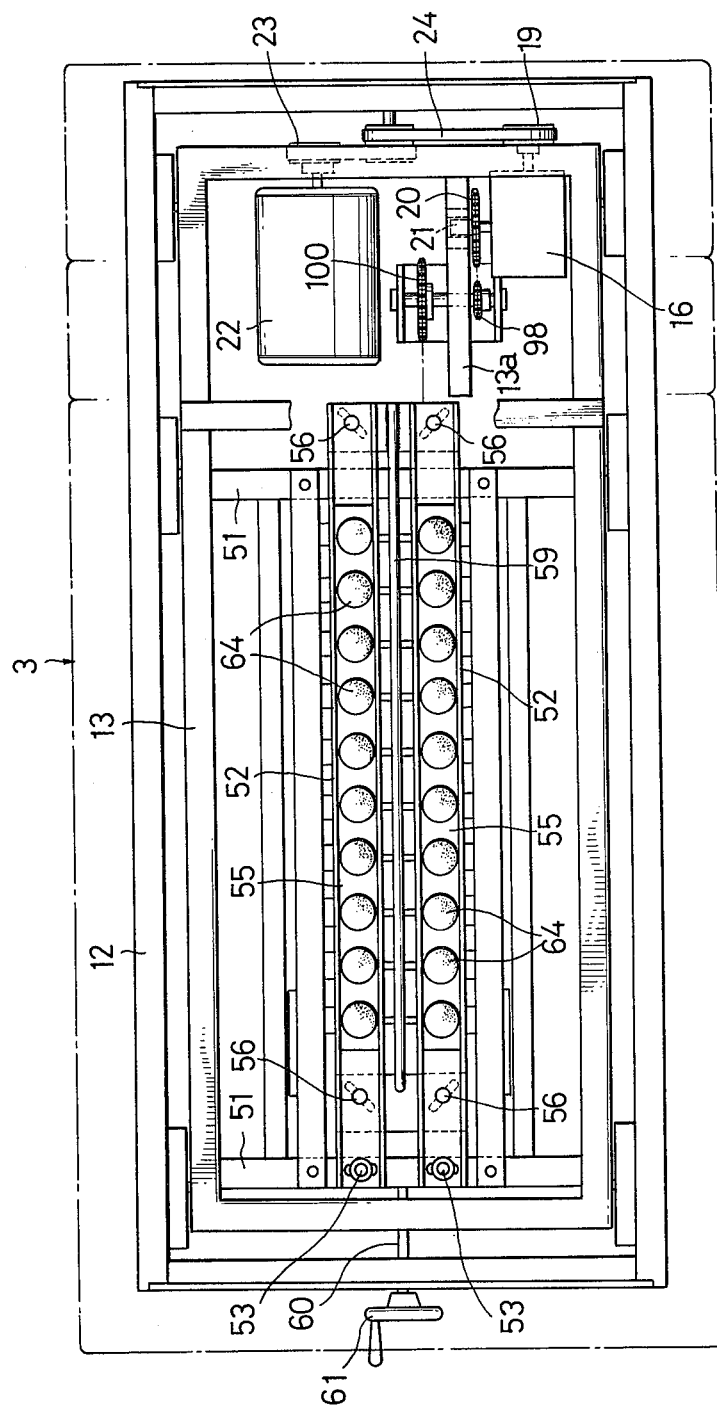
FIG. 3 is a plan view of the main part of the machine from which the mobile bed has been removed.
Figure 4:
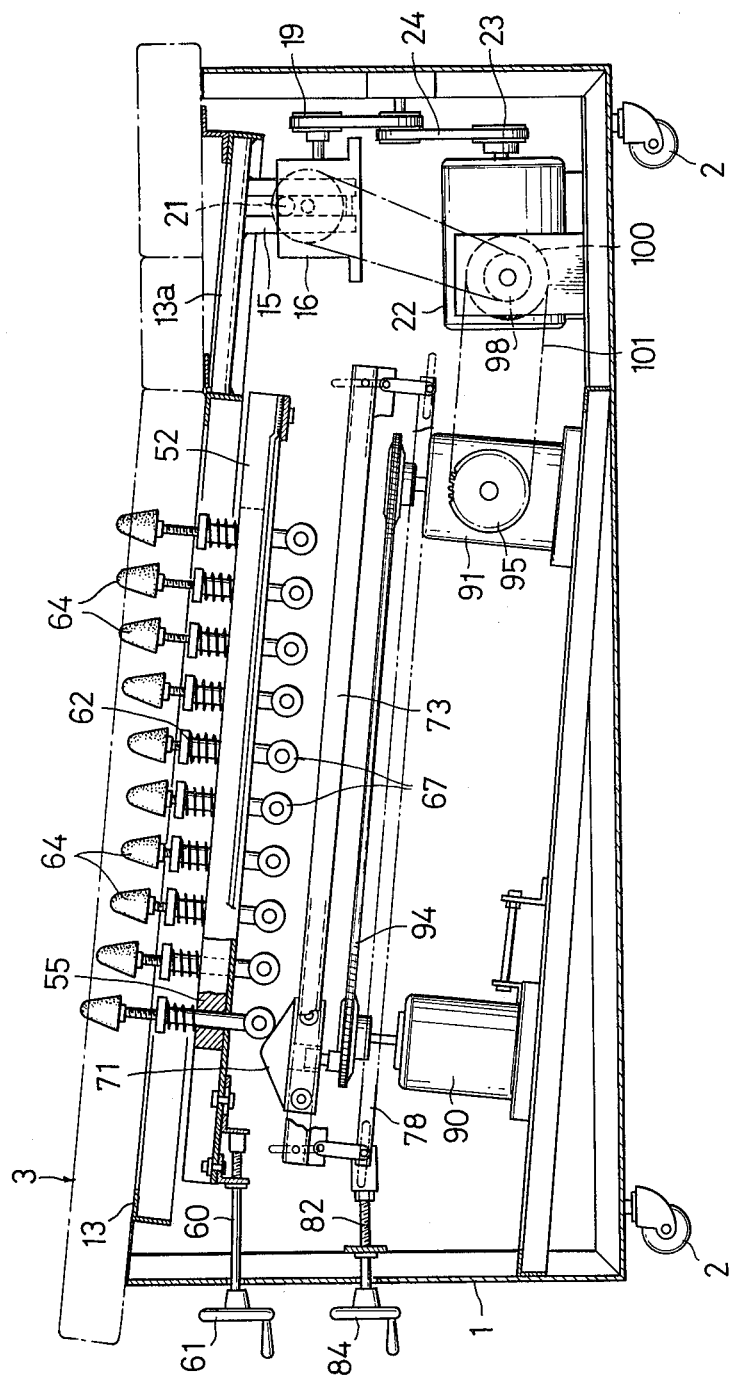
FIG. 4 is a side view of a partial cross-section of FIG. 3.
Figure 5:
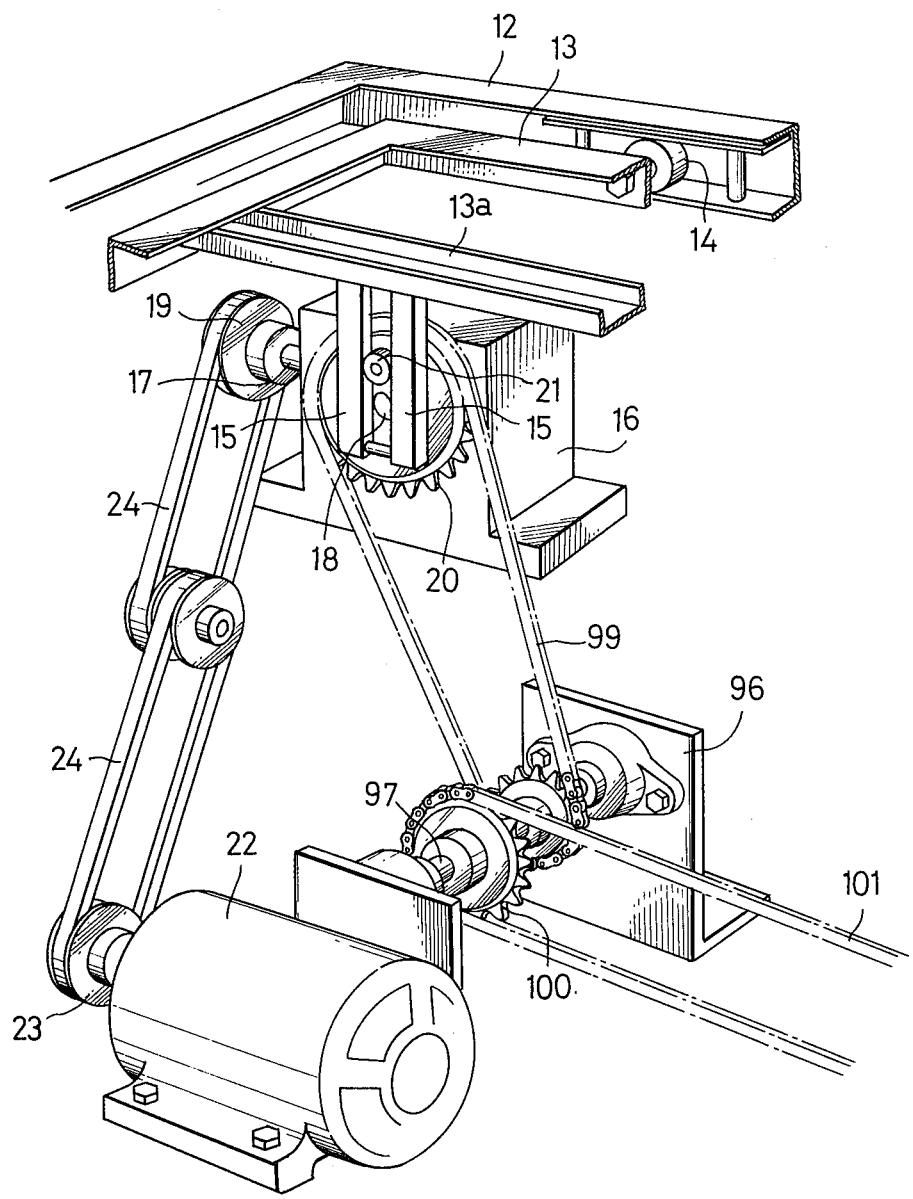
FIG. 5 is an oblique view showing the driving mechanism of the mobile bed.

The driving mechanism of the mobile bed 3 will now be explained with reference to FIGS. 3 and 5. Inside the machine base 1 are provided two channel-shaped guide rails 12 parallel to the longitudinal direction, the said guide rails 12 facing each other with respect to their open ends. Rollers 14 attached to the outside of the mobile frame 13 connected to the mobile bed 3 are inserted into the said guide rails 12 thus supporting the mobile bed 3. The connecting rod 13a provided on the said frame 13 has two support plates 15 with a predetermined space therebetween; the plate being joined with a pin at the ends. A gear box 16 is provided on the machine base 1 and has rotating axes 17, 18 interconnected inside the box and extending in different directions; a pulley 19 is attached to the first rotating axis, while a chain gear 20 is attached to the second axis 18. A roller 21 is eccentrically attached to the said chain gear 20 and is inserted into a gap formed by the said support plates 15 to be joined to the plates.

22 is a motor attached to the machine base 1 which turns the rotating axes 17, 18 by the pulley belt 24 which is hung around the driving wheel 23 and a pulley freely rotating midway to the pulley 19 of the said gear box 16.

When the said motor 22 is on, the belt 24 hung around the driving wheel 23 turns the pulley 19 of the gear box 16 and also turns the rotating axis 18 which is connected and turned inside the gear box. The roller 21 of the chain gear 20 provided on the said rotating axis 18 reciprocally moves the support plates 15 joined to the mobile frame 13 in the horizontal direction for a distance equivalent to the eccentric amount of the roller. Accordingly, the mobile frame 13 reciprocally moves, supported by the guide rails 12 of the machine base to move the mobile bed 3, joined to the said mobile frame 13, in the longitudinal direction.

Figure 6:
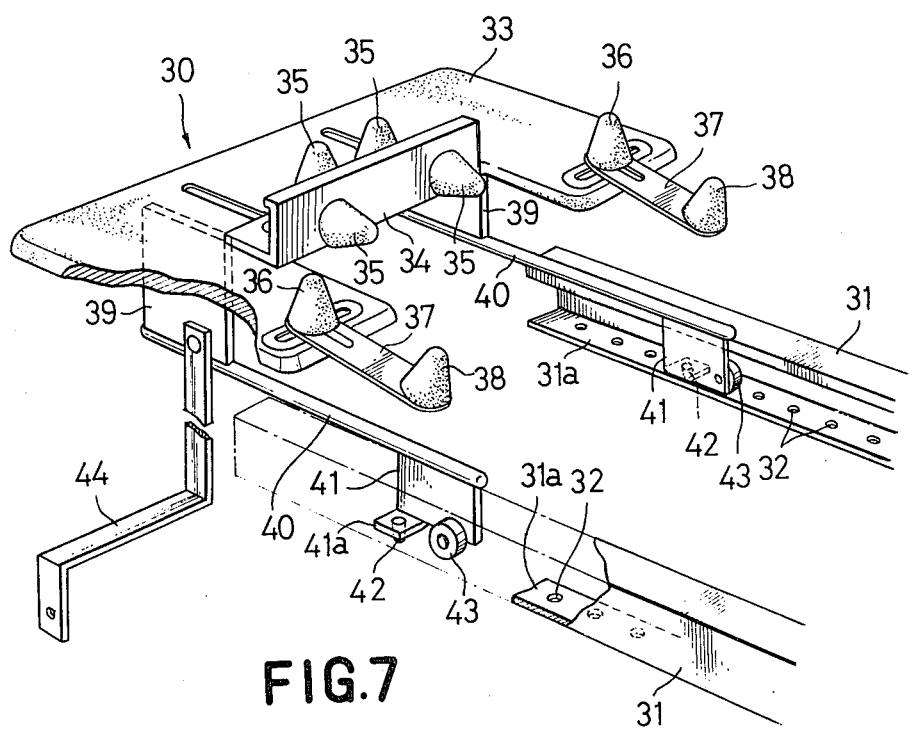
FIG. 6 is an oblique view showing the head-rest.
Figure 7:
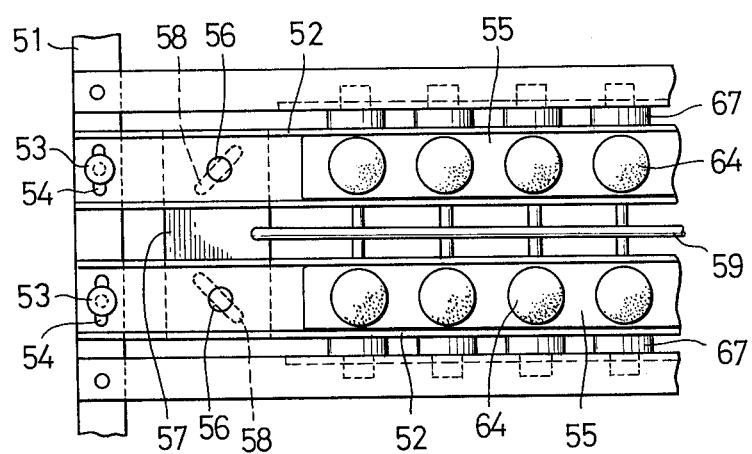
FIG. 7 is a plan view showing a group of pressure members.
Figure 8:
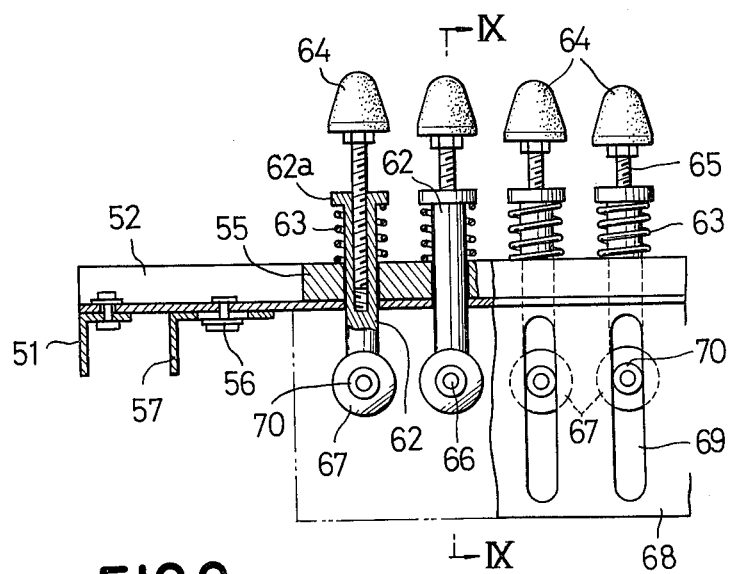
FIG. 8 is a side view of a partial cross-section of FIG. 7.
Figure 9:
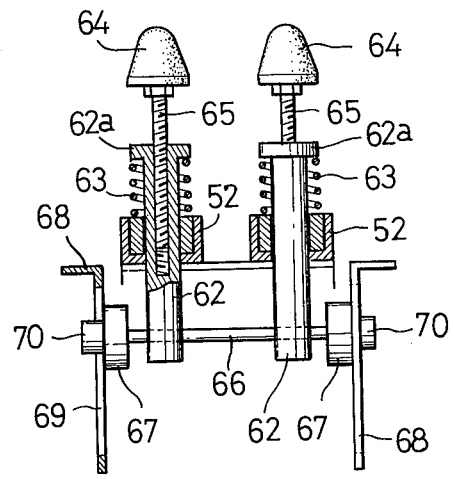
FIG. 9 is a partially fragmentary front view along the line IX—IX of FIG. 8.
Figure 10:
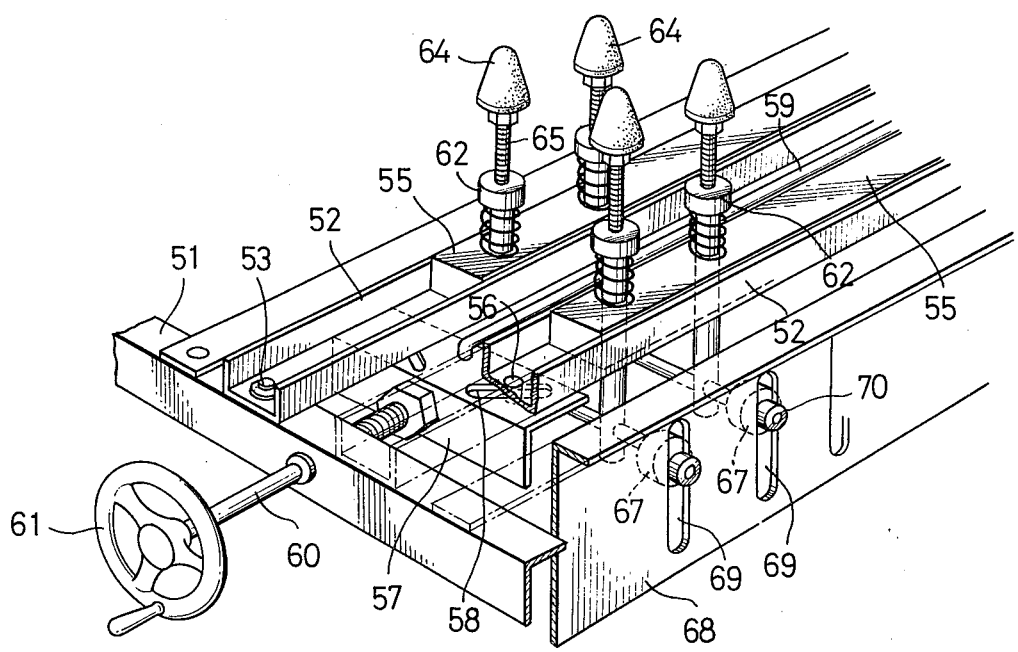
FIG. 10 is an oblique view of a group of pressure members.

The head-rest 30 will now be explained with reference to FIG. 6. Inside the hole 11 of the said mobile bed 3 in its longitudinal direction are provided two channel-shaped guide grooves 31 with their open ends facing each other and with a plurality of small bores 32 continuously provided on the groove plate 31a positioned on the bottom side. 33 is a pillow stand provided with a head-rest 34 which is freely adjustable parallel to the direction of the movement of the said mobile stand 3 at the attachment portions. On this headrest 34 are provided projections 35 made of rubber or a similar material. On both sides of the said pillow 33 are also provided projections 36 to press the shoulders, and projections 38, at the end of the support plates 37 which turn in respect to the said projections 36. With adjustable butterfly screws attached to the lower ends of the pillow, it is possible to easily change the position of attachment without using any tools.

Beneath the said pillow stand 33 are provided two pulling rods 40 parallel to the said guide grooves 31 via the support plates 39 with stoppers 41 provided on the said pulling rods. The said stoppers 41 have bent parts 41a bent in the horizontal direction and attached with the engagement pins 42. 44 is a connecting arm attached to one of the support plates 39 of the said pillow stand 33.

The stoppers 41 of the pulling rods 40 of the said pillow stand 33 are inserted into the opening of the guide grooves 31 and engagement pins 42 fit into one of the small bores 32 of the guide groove to fix the pillow stand. The pillow stand is moved by lifting the stand up and removing the engagement pins 42 of the stopper from the small bores 32, and again interlocking the engagement pins 42 and the small bores 32 at an arbitrary position to fix the pillow stand.

The aforementioned groups of pressure members 50 will now be explained with reference to FIGS. 3, 4 and 7 to 11. Two cross-pieces 52 are attached to the shelves 51 fixed to both sides of the machine base 1 parallel to the moving direction of the said mobile stand 3 and in such a fashion as to enable a change of the intervals of attachment. The joint where the said cross-pieces 52 and the shelves 51 are connected is housed within the long holes 54 bores in a direction perpendicular to the longitudinal direction of the cross-pieces.

The said cross-pieces 52 are shaped like a channel with their open ends facing upward and housing the cross-pieces 55 therein. On the lower surfaces of the two ends of the cross-pieces are provided protruding engagement pins 56. 57 are the operating boards placed protrudingly over the positions of the said engagement pins 56 where two holes 58 inclined in a direction different from the longitudinal direction of the cross-pieces are bored. In these inclined holes are inserted the said engagement pins 56 to the lower end of which are slidably attached the operating boards and cross-pieces joined together. The two operating boards 57 are connected to each other by the connecting rod 59 with an operating axis 60 screwed into the shelf 51 of one of the operating boards 57 and also rotatably to the machine base 1. To the end of the operating axis 60 is attached a handle 61.

When the operating axis 60 is turned by the said handle 61, the two operating boards 57, interlocked by the connecting rod 59 and joined to the operating axis, move in a direction parallel to the longitudinal direction of the cross-pieces 52. The motion of the operating boards causes the cross-pieces 52 to move in a direction perpendicular to the longitudinal direction of the cross-pieces away from the operating board and the intervals between the cross-pieces are freely changeable.

On the cross-pieces 55 housed within the said cross-piece members 52, there are loosely supported a plural number of cylindrical pressure rods 62 extending vertically through the said cross-pieces and cross-piece members, the top of which extends from the flange 62a, and springs 63 are fixed between the cross-pieces and the said flanges. Inside the pressure rods 62 are provided female screws to receive the screw rods 65 of the pressure members 64.

The said pressure member 64 has a round-shaped tip and is formed of rubber or a similar material. The screw rod 65 is fixed at its lower end. Through the lower ends of the said pressure rods 62 are loosely inserted connecting axes 66 through a pair of cylinders facing each other in a direction perpendicular to the longitudinal direction of the cylinder (see FIG. 9). The rollers 67 are attached to both ends of the said connecting rods 66. On the said machine base 1 are provided two guide plates 68 extending in the perpendicular direction and close to the said rollers 67. In the positions corresponding to each of the connecting rods 66 are bored long holes 69 extending vertically. In the said holes 69 are inserted the rollers 70 provided at the end of the said connecting axes, the said rollers 67 being positioned inside the guide plates 68.

There is provided a movable angular cam 71 for pushing the cylindrical body up to engage with rollers 67 of the said pressure rods 62. Further, to the two side plates 72, provided parallel to the cross-pieces of the said pressure member groups 50 fixed to the said machine base 1, are attached guide rails 73 with changable positions of attachment. (See FIG. 11). To the guide rails 73 are provided pins 74 which are inserted into the long holes 75 bored in the vertical direction and joined through the side plate. To the guide rails 73 are attached connecting pieces 76 via axes 77 vertically and close to the both sides. To the ends of the connecting pieces 76 are joined rods 78 parallel to the guide rails via axes 79, the said axes 79 extending outward and inserted through the long holes 80 bored horizontally in the side plates 72.

Of the axes 79 connecting the said connecting pieces 76 and the connecting rods 78, one is joined with the opposite connecting piece (not shown). To the metal fixture 81 provided on the said axis, an operating rod 82 is attached in a direction parallel to the said guide rails 73. The center portion of the said operating rod 82 is screwed into the machine frame 83 fixed to the machine base, while the rest of the rod is screwed to the machine base. The rod now can freely rotate and extends outside the machine base with a handle 84 attached to its end.

Figure 11:
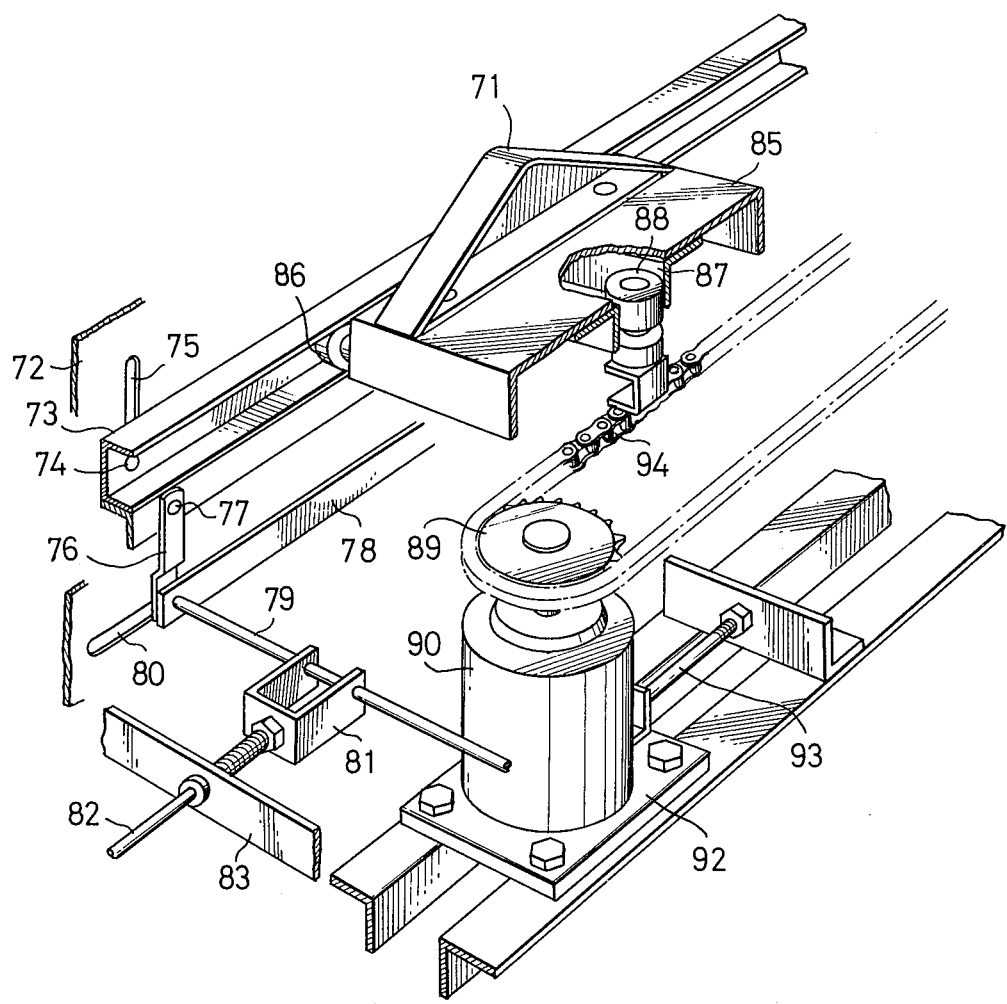
FIG. 11 is a partially fragmentary oblique view showing the driving mechanism of an angular cam.
Figure 14:
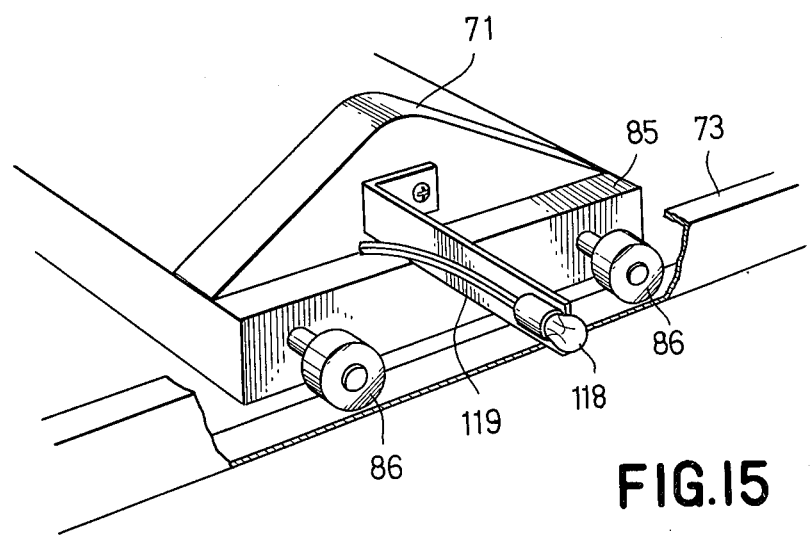
FIG. 14 is a partially fragmentary oblique view showing the angular cam attached with a small lamp and FIG. 15 is a partially fragmentary oblique view showing various parts of the automatic diagnostic mechanism.
Figure 15:
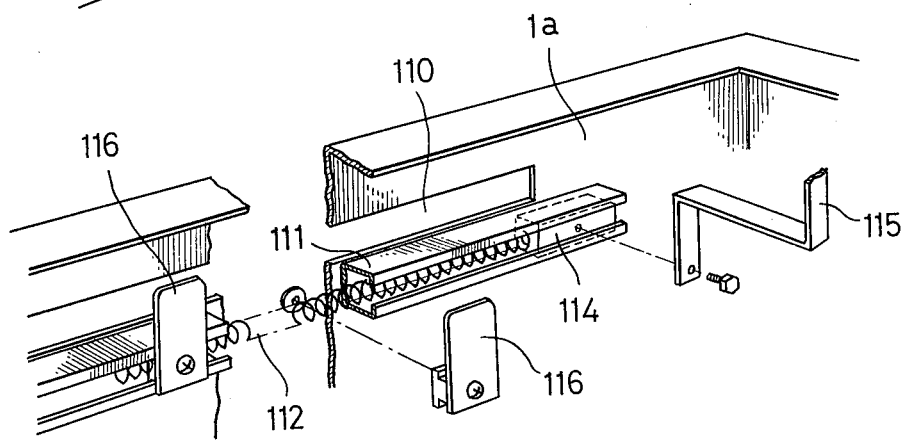

The said guide rails 73 are channel-shaped with their open ends facing each other, and the rollers 86 are inserted into the guide rails to movably join the cam attachment plates parallel to the guide rails. The aforementioned angular cam 71 becomes engaged with the said pressure rods 62 and the rollers 67. If it has the same width as the cam attachment plate, it then simultaneously engages with the said two rollers. In the present embodiment, there is only one angular cam 71 provided at the position where it becomes engaged with a roller. In FIG. 11, the second angular cam is not shown.

Beneath the said cam attachment plate 85 is provided a guide groove 87 in a direction perpendicular to the movement of the cam attachment plate, and a roller 88 is inserted in this guide groove 87. There are provided bearing stands 90, 91 having chain gears 89 rotating in the horizontal direction on the machine base 1 beneath the said guide rails 73 on both sides of the pressure member groups 50 with one of the bearing stands 90 being fixed on the base plate 92, the said base plate being provided with an adjusting screw 93 for adjusting the position of attachment between the machine base.

A chain 94 is hung over and around the said chain gears 89 and the roller 88 housed within the guide groove 87 of the said cam attachment plate 85 is fixed to the said chain 94 to allow the cam attachment plate 85 to reciprocally move by the movement of the chain. The said bearing stand 91 also acts as a gear box and is attached with a chain gear 95 to the rotating axis extending from the side wall and interlocked by the bevel gear, etc. There is another chain 99 hung around the chain gear 20 provided to reciprocally drive the said mobile stand 3 and the chain gear 98 provided on the gear axis 97 screwed over the bearing plate 96 provided on the machine base 1; there is still another chain 101 hung over the second chain gear 100 provided on the said axis 97 and the chain gear 95 of the said bearing stand 91, all to reciprocally move the mobile stand 3 and the angular cam 71 by the said motor 22.

The handle 84 turns the operating rod 82 so that the metal fixture 81 interlocked to the operating rod and the axis 79 run parallel to the longitudinal direction of the guide rails 73. As the end of the axis 79 is inserted into the lateral holes 80 bored in the guide plates 68, the connecting pieces 76, joined to the axis 79, become inclined when the axis 79 moves horizontally and the end axes 77 of the connecting piece become lowered. This causes the guide rails 73 to slidably move as the pins 74 extending outward from the guide rails 73 become inserted into the longitudinal holes 75 and also to become lowered by the inclined position of the connecting pieces. The said connecting pieces 76, which are joined to one guide rail 73, are joined via the connecting rod 78, thereby securing the vertical movement of the guide rail 73.

The groups of pressure means 50 may be adjusted with respect to their height by turning the screw rods 65 of the pressure member 62 extending from each unit 60 so as to meet the contour of the patient's spine when the patient is lying down on the mobile bed 3. (See FIG. 4). The patient places his head on the head-rest 30 and his hip on the hip-rest 3a of the mobile bed 3.

The motor 22 then drives the mobile stand 3, thus causing the two sides of the patient's spine to move reciprocally over the said groups of pressure members 50 and to receive a massage. At the same time, as the rotational force of the motor drives the chain 94 turning in the horizontal direction and the roller 88 joined to the chain 94 is in the guide groove 87 of the cam attaching plate 85, the movement of the chain 94 moves the said cam attachment plate parallel to the longitudinal direction of the pressure means and the angular cams 71 push upward the rollers 67, provided on the connecting axis 66 at the lower ends of the pressure rods 62. Thus, the pressure means 64 are pressed upward by the movement of the angular cams to impart the pressure effect to the patient.

When the roller 88 of the said chain 94 reaches one of the chain gears 89, the angular cam 71 starts movement to the reverse direction. When the roller 88 is turning around the chain gear 89, the roller 88 slides inside the guide groove 87 and the cam attachment plate 85 stands still. By turning the upper handle 61, one of the two handles protruding from out of the machine base, it is possible to adjust the intervals between pressure means groups; and by turning the other handle 84, the height of the angular cam 71 may be adjusted. Therefore, it is possible to optimumly treat the patients and control the SHIATSU pressure being applied.

The automatic diagnosis apparatus for diseases of visceral organs will now be explained with reference to FIGS. 12 to 15. There is provided a guide window 110 on the outer wall 1a of the aforementioned machine base 1 parallel to the guide rails 71 and at a position where the angular cam 69 conducts a reciprocal movement within the said guide rails 71. Beneath the guide window 110 is attached a guide groove 111. The said guide groove 111 is made of a channel-shaped material and it should be fixed to the said head-rest 30 at one end and extend to a position where the connecting arm 44 joined thereto reaches the utmost end of the machine base.

In the said guide groove 111 is inserted a flexible means 112 at both ends of which are attached a slider 113 and a metal stopper 114. The slider 113 is joined to the support arm 44 of the said head-rest 30 while the metal stopper at the other end is joined to the fixture member 115 provided on the fixed part in the machine base. Accordingly, the said flexible member 112 is fixed on the stopper side 114 and is extended or contracted on the side of the slider 113 as it moves inside the guide groove 111.

The said flexible member 112 is a coil spring and is fixed in such a way that the indicator plates 116 can move along the periphery of the guide groove 111 at a predetermined interval. The indicator plates carry the names of various organs where diseases may be detected printed at the points corresponding to the points along the spine when the patient's lumbar vertebrae is placed at the standard point 117 provided at the end of the said mobile stand 3 and his head is on the head-rest 30. As these points do not change their relative positions irrespective of the different heights of the individual patients, the said indicator plates 116 do not change their relative positions when the flexible members extend or contract by the slider 113 moving along with the head-rest 30.

On the side facing the guide window 110 of the said angular cam 69 is provided a pointer 119 having a small lamp 118, the said lamp 118 being inside the guide window 110 of the outer wall 11a of the machine base to facilitate interpretation of the symbols or letters on the indicator 116. If there is felt any discomfort as the angular cam 69 pushes the pressure member 62, the motor 22 is stopped and the indicator is read at the point where the end of the pointer 119 and the indicator 116 meet. Therefore, the small lamp may be red or any other color.

When the head-rest 30 is moved to meet the height of a patient, the flexible member 112 is contracted or extended by the connecting arm 44 interlocking with the head-rest and the position of the indicators 116 is adjusted. The angular cam 69 pushes the pressure members 62 upward and if the patient feels any pain or discomfort at any particular point, the angular cam is stopped and the indicator 116, which agrees with the pointer 119, is read and the organ which is malfunctioning is detected by the type of symbols on the said indicator.

It will be easily understood that the apparatus of the present invention is effective in automatically detecting the diseases of visceral organs and in giving massages to the areas around the spine.

What is claimed is:

1. An automatic disease-detecting treatment apparatus of the spine comprising a machine base, a mobile bed which moves in the longitudinal direction on said machine base, an adjustable pillow stand, a head-rest located on said pillow stand, which pillow stand and head-rest are located at one end of said mobile bed, two adjustable cross members mounted at intervals parallel to the longitudinal movement of said mobile bed, a plurality of cylindrical pressure members of adjustable mounting height which form covered pressure members at the tips, an angular cam which engages itself with said pressure members at the lower surface of said pressure members and which moves longitudinally in the direction of the movement of said bed, a flexible member fixed at one end to said head-rest of said mobile bed and at the other to said machine base, a plurality of indicator plates on said flexible member arranged in accordance with the positions of human organs, showing each of these organs, and a pointer provided at said angular cam, which moves longitudinally at the back of the said flexible member.

2. An automatic disease-detecting treatment apparatus of the spine as claimed in claim 1, in which said mobile bed is made movable by means of a mobile frame containing rollers provided outside of said mobile frame, two guide rails provided longitudinally parallel to each other inside of said machine base and wherein said rollers are inserted into the two guide rails to effect the movement of the mobile bed.

3. An automatic disease-detecting treatment apparatus of the spine as claimed in claim 2, wherein two supporting plates are mounted vertically on said mobile frame and a roller provided eccentrically at a chain gear of a rotating axis inserted into the gap formed between said two space supporting plates is employed to move the mobile bed and a motor, said motor functioning by rotating said chain gear which causes the roller between said two space supporting plates to move the mobile frame along the guide roller in a longitudinal direction.

4. An automatic disease-detecting treatment apparatus of the spine as claimed in claim 1, wherein two pulley rods are connected at said pillow stand in a direction parallel to said guide grooves, stoppers located at the edges of the two pulley rods containing bores provided therein so as to contact the guide grooves, small bores continuously provided in said guide grooves, and engagement pins which engage the stoppers with the guide grooves through the said bores, thereby making the pillow stand adjustable along the length of the mobile bed.

5. An automatic disease-detecting treatment apparatus of the spine as claimed in claim 4 in which pressure members are provided in the center as well as on both sides of said pillow stand.

6. An automatic disease-detecting treatment apparatus of the spine as claimed in claim 1 in which cross pieces are housed in said two cross members provided parallel to the moving direction of said mobile bed; operating boards located over the ends of said cross members; engagement pins located in two holes, one over each of the ends of said cross members connecting the operating boards to said cross members, said holes being elongated in a direction different than the longitudinal direction of said cross pieces; a connecting rod connecting the two operating boards so that they may be moved simultaneously; a handle mounted on an operating axis provided on one of said operating boards in such a way that it protrudes from said machine base, and wherein intervals of said cross pieces are adjustable outside of said machine base, said cross pieces being adjustable at different mounting intervals by means located outside of said machine base.

7. An automatic disease-detecting treatment apparatus of the spine as claimed in claim 1 wherein the two cross members contain two cross pieces housed therein in a direction parallel to the movement of the mobile bed, a plurality of cylindrical pressure members extending vertically from said cross pieces containing flanges formed at the upper protruding parts of said cylindrical pressure members, said members being loosely supported by said cross pieces and cross members through holes in said cross pieces and cross members so that they may slide freely through said holes, fixed springs located around said cylindrical pressure members located between said flanges and cross pieces; said cylindrical pressure members each comprised of a cylinder and screw rod inserted therein; said cylinders containing female screws to receive said screw rods and wherein said screw rods are screwed into said cylinder and protrude upward from said cylinders, connecting rods located underneath said cross members which extend through holes located at the bottom of said cylinders of said cylindrical pressure members so that the rods may freely rotate therethrough; said rods extending in a direction perpendicular to the movement of said mobile bed and positioned so that each rod connects two cylinders located next to each other on said cross members and rollers connected to the ends of said connecting rods.

8. An automatic disease-detecting treatment apparatus of the spine as claimed in claim 7 in which said pressure member has a round shaped tip and is formed of rubber or a material similar to rubber.

9. An automatic disease-detecting treatment apparatus of the spine as claimed in claim 1 in which said machine base has two single plates containing guide rails attached to the sides thereof, said angular cam having cam attachment plates connected thereto with rollers located thereupon, said angular cam being made movable by inserting the said rollers located on the cam attachment plates into said guide rails; said cam attachment plate further containing a guide groove perpendicular to the movement of said cam attachment plate, said cam being actuated by means of a roller which fits into said guide groove, and wherein the roller is attached to a chain assembly connecting two gears, said chain and gear assembly being provided inside of said machine base.

10. An automatic disease-detecting treatment apparatus of the spine as claimed in claim 9 wherein the height of the angular cam is made adjustable by means of pins provided at said guide rails inserted into elongated vertical holes provided in said side plates, connecting pieces mounted at the ends thereupon to said guide rails by means of a connecting rod which is inserted into two elongated horizontal holes provided on said side plates, a metal fixture located on the said connecting rod, an operating rod protruding through said machine base and connecting said metal fixture and a handle connected to the end of the operating rod protruding out of said machine base for adjusting said angular cam.

11. An automatic disease-detecting treatment apparatus of the spine as claimed in claim 1 in which said flexible member is a coil spring, a guide groove for housing said flexible member, a metal stopper fixed at one end of said guide groove, a slider located at the other end of said guide groove and a support arm of said head-rest which connects the slider within said guide groove to the said head-rest.

12. An automatic disease-detecting treatment apparatus of the spine as claimed in claim 1 in which said indicators are arranged on said flexible member in accordance with the locations of each human organ, inside a guide window formed at an outer wall of said machine base parallel to said flexible member.

13. An automatic disease-detecting treatment apparatus of the spine as claimed in claim 1 in which said pointer is connected to said angular cam, and a small lamp is mounted to said pointer's edge inside said guide window of said outer wall so that when said angular cam is stopped, said indicators can be interpreted by means of said lamp.

* * * * *